United States Patent
Schleif et al.

(10) Patent No.: US 9,719,816 B2
(45) Date of Patent: Aug. 1, 2017

(54) FITTING FOR POSITIONING A PROBE IN A HOT GAS PATH OF A GAS TURBINE ENGINE

(71) Applicant: General Electric Company, Schenectady, NY (US)

(72) Inventors: Kurt Kramer Schleif, Greenville, SC (US); Zachary John Snider, Simpsonville, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 409 days.

(21) Appl. No.: 14/474,884

(22) Filed: Sep. 2, 2014

(65) Prior Publication Data
US 2016/0061638 A1 Mar. 3, 2016

(51) Int. Cl.
| | |
|---|---|
| *G01D 21/00* | (2006.01) |
| *G01D 11/30* | (2006.01) |
| *G01N 33/00* | (2006.01) |
| *G01D 11/24* | (2006.01) |
| *G01N 1/22* | (2006.01) |
| *G01M 15/14* | (2006.01) |
| *F01D 21/00* | (2006.01) |

(52) U.S. Cl.
CPC ............ *G01D 11/30* (2013.01); *G01D 11/245* (2013.01); *G01N 33/0009* (2013.01); *F01D 21/003* (2013.01); *G01M 15/14* (2013.01); *G01N 1/2247* (2013.01); *G01N 2001/2285* (2013.01); *G01N 2201/021* (2013.01); *G01N 2201/0227* (2013.01)

(58) Field of Classification Search
CPC ......... G01N 1/2247; G01N 2001/2285; G01N 33/0009; G01N 33/0027; G01N 2201/021; G01N 2201/0227; G01M 15/14; F01D 21/003; F01D 25/285; G01D 11/30; G01D 11/245
USPC ................... 73/31.05, 112.01, 863.85, 866.5
See application file for complete search history.

(56) References Cited

U.S. PATENT DOCUMENTS

| | | | |
|---|---|---|---|
| 5,101,165 A | * 3/1992 | Rickards | .............. G01B 7/14 |
| | | | 324/662 |
| 5,349,850 A | * 9/1994 | Young | .............. G01B 11/00 |
| | | | 73/112.01 |
| 6,776,524 B2 | 8/2004 | Park et al. | |
| 6,857,776 B2 | 2/2005 | Park | |
| 8,342,019 B2 | * 1/2013 | Hokamura | ........ G01N 33/0006 |
| | | | 73/24.06 |

* cited by examiner

*Primary Examiner* — Benjamin Schmitt
(74) *Attorney, Agent, or Firm* — Eversheds Sutherland (US) LLP

(57) ABSTRACT

A fitting for positioning a probe in a hot gas path within a casing of a gas turbine engine is disclosed herein. The fitting includes a main body attachable to the casing opposite the hot gas path. The main body includes an internal bore and one or more cooling holes in communication with the internal bore. A compliant seal is positionable within the internal bore. In addition, a follower is positionable within the internal bore adjacent to the compliant seal. Moreover, the fitting includes a fastener configured to mate with the main body. In this manner, the follower deforms the compliant seal about the probe within the main body to secure and seal the probe within the main body.

19 Claims, 4 Drawing Sheets

FITTING FOR POSITIONING A PROBE IN A HOT GAS PATH OF A GAS TURBINE ENGINE

FIELD OF THE DISCLOSURE

The disclosure generally relates to a fitting and more particularly relates to a fitting for positioning a probe in a hot gas path of a gas turbine engine.

BACKGROUND

The use of ceramic probes is highly desirable downstream of combustors where the use of probes made from metal is not possible. Ceramic probes generally do not require cooling like metal components and are therefore more efficient. Ceramic probes are also cheaper than metal probes and generally last longer. Moreover, ceramic probes may be lighter and more reliable than metal probes. However, holding ceramic probes in a hot, high-flow, highly dynamic gas path may be difficult. In addition, creating a seal around a ceramic probe can be problematic, particularly when transitioning from a ceramic probe to a metal tube. Current sealing techniques are highly susceptible to leaks and are prone to damage the ceramic probe.

SUMMARY

Some or all of the above needs and/or problems may be addressed by certain embodiments of the fitting disclosed herein. The fitting may be used for positioning a probe in a hot gas path within a casing of a gas turbine engine. The fitting may include a main body attachable to the casing opposite the hot gas path. The main body may include an internal bore and one or more cooling holes in communication with the internal bore. A compliant seal may be positionable within the internal bore. In addition, a follower may be positionable within the internal bore adjacent to the compliant seal. The fitting also may include a fastener configured to mate with the main body. In this manner, the follower may deform the compliant seal about the probe within the main body to secure and seal the probe within the main body.

In another embodiment, a method of positioning a probe in a hot gas path within a casing of a gas turbine engine is disclosed. The method may include attaching a main body to the casing opposite the hot gas path. The main body may include an internal bore and one or more cooling holes in communication with the internal bore. The method also may include positioning the probe within the internal bore, a compliant seal within the internal bore about the probe, and a follower within the internal bore about the probe and adjacent to the compliant seal. The method further may include adjusting a fastener attached to the main body. Moreover, the method may include deforming the compliant seal about the probe within the main body to secure and seal the probe within the main body.

In another embodiment, an assembly for taking measurements in a hot gas path within a casing of a gas turbine engine is disclosed. The assembly may include a ceramic probe and a fitting for positioning the ceramic probe in the hot gas path within the casing of the gas turbine engine. The fitting may include a main body. The main body may include a first end and a second end. The first end may be attachable to the casing of the gas turbine engine opposite the hot gas path. The main body also may include an internal bore extending from the first end to the second end. At least a portion of the ceramic probe may be positionable within the internal bore. The main body also may include one or more cooling holes in communication with the internal bore. The fitting also may include a compliant seal positionable within the internal bore about the ceramic probe, a follower positionable within the internal bore about the ceramic probe and adjacent to the compliant seal, and a fastener having a first end configured to mate with the second end of the main body. The follower may deform the compliant seal to secure and seal the ceramic probe within the main body.

Other features and aspects of the fitting will be apparent or will become apparent to one with skill in the art upon examination of the following figures and the detailed description. All other features and aspects, as well as other system, method, and assembly embodiments, are intended to be included within the description and are intended to be within the scope of the accompanying claims.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Figure 1:
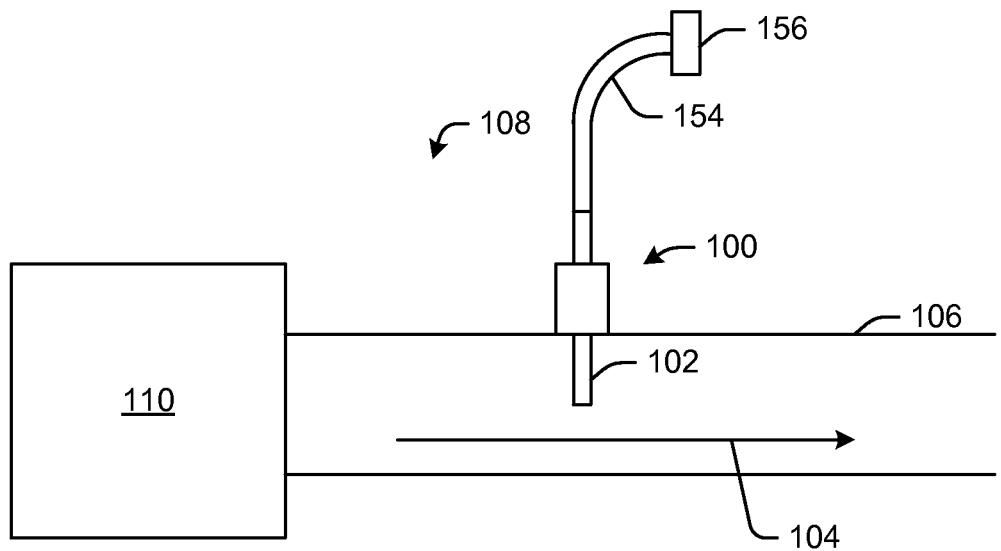
FIG. 1 schematically depicts a fitting in accordance with one or more embodiments of the disclosure.
Figure 2:
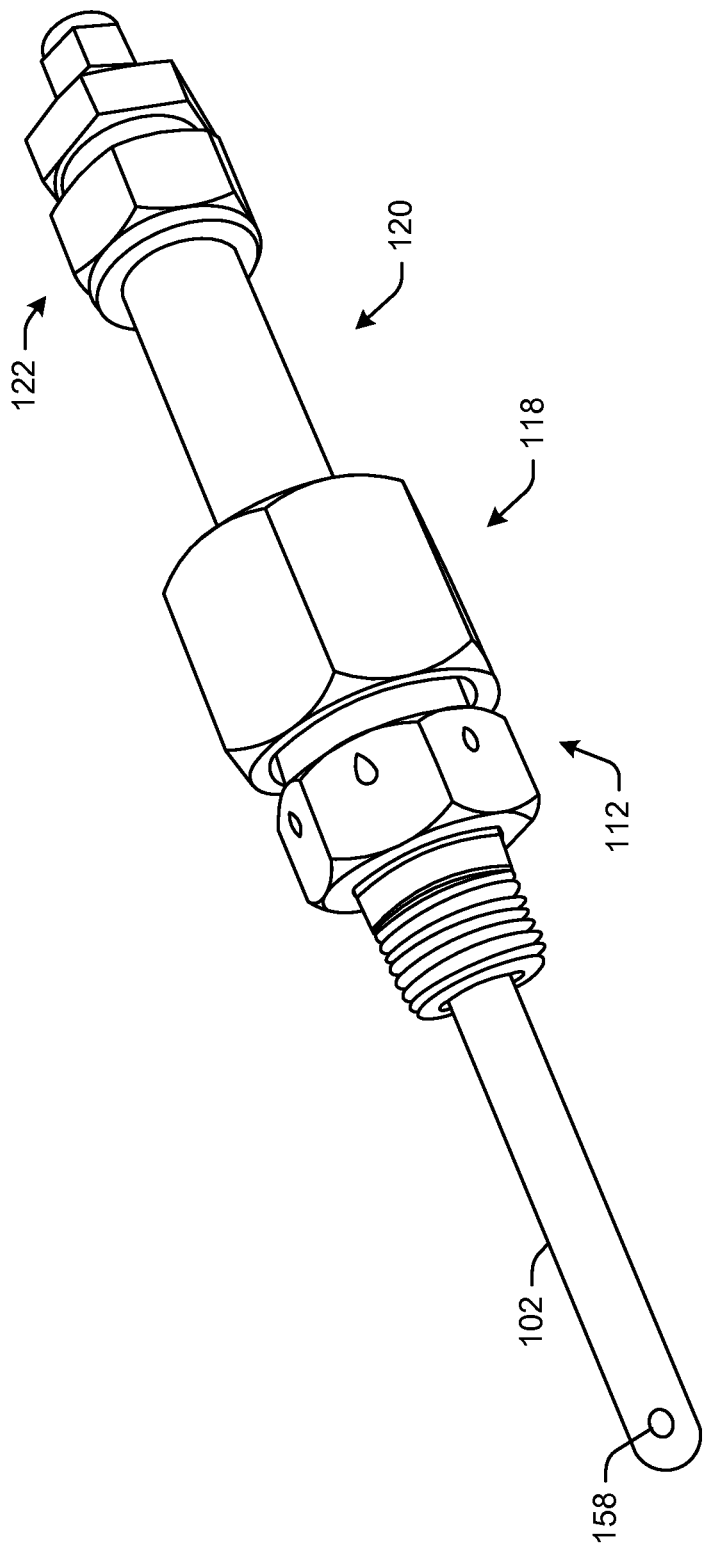
FIG. 2 schematically depicts a fitting in accordance with one or more embodiments of the disclosure.
Figure 3:
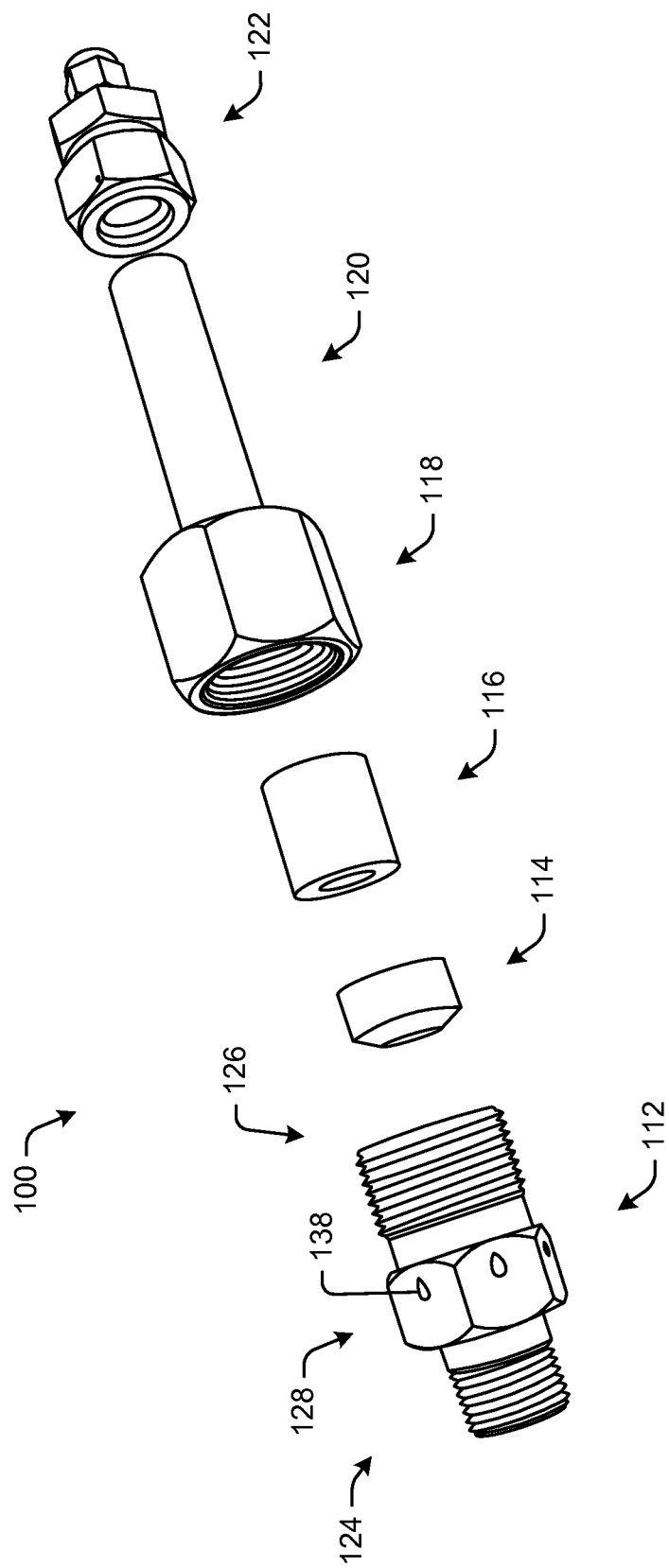
FIG. 3 schematically depicts an exploded view of a fitting in accordance with one or more embodiments of the disclosure.
Figure 4:
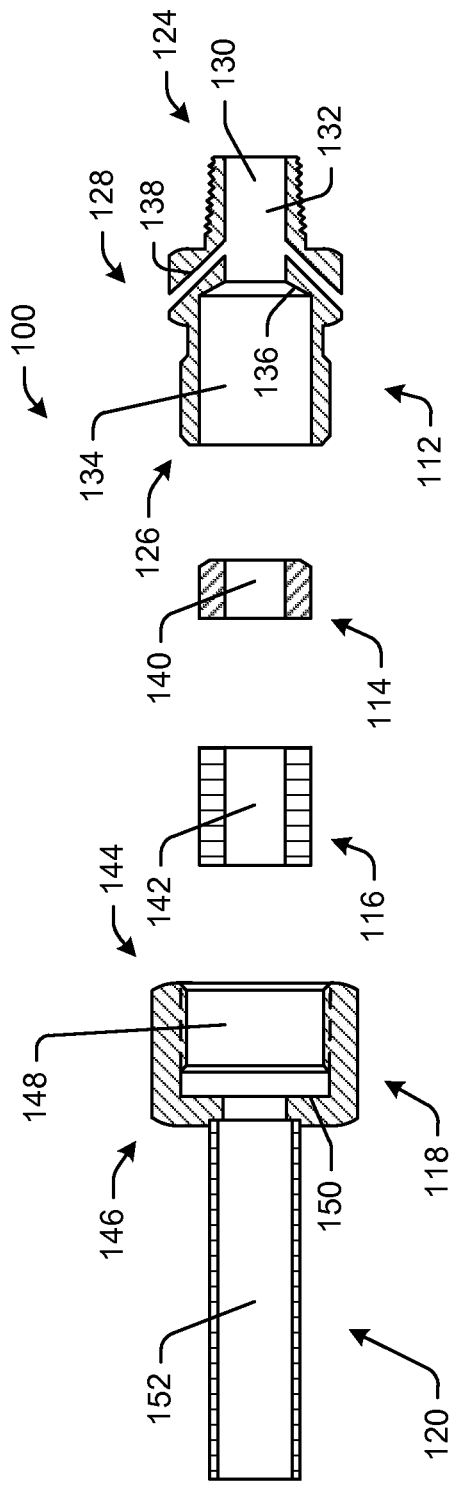
FIG. 4 schematically depicts a cross-sectional view of a fitting in accordance with one or more embodiments of the disclosure.

FIGS. 1-4 schematically depict an embodiment of a fitting 100 for positioning a probe 102 in a hot gas path 104 within a casing 106 of a gas turbine engine 108. For example, the probe 102 may be positioned downstream of a combustor 110 of the gas turbine engine 108. The fitting 100 may include, among other things, a main body 112, a compliant seal 114, a follower 116, a fastener 118, a tube 120, and/or a compression fitting 122.

In some instances, the main body 112 may include a first end 124 and a second end 126. The first end 124 of the main body 112 may be attachable to the casing 106 of the gas turbine engine 108 opposite the hot gas path 104. That is, the main body 112 may be attached to an outside portion of the casing 106. For example, the first end 124 of the main body 112 may include threads or the like. Moreover, the main body 112 may include a middle portion 128 (such as a hex head or the like) for tightening the main body 112 to the casing 106. In some instances, the main body 112 may be attached to the outside portion of the casing 106 downstream of the combustor 110. In this manner, the fitting 100 may secure the probe 102 within the hot gas path 104. In addition, the fitting 100 may form a seal about the probe 102.

The main body 112 also may include an internal bore 130 extending from the first end 124 of the main body 112 to the second end 126 of the main body 112. The probe 102 may be at least partially housed within the internal bore 130. In some instances, the probe 102 may be positionable within the internal bore 130. For example, the internal bore 130 may include a first portion 132 about the first end 124 of the main body 112 that includes a diameter that is about the same size as the probe 102. In some instances, the outer diameter of the probe 102 may be about the same size or slightly smaller than the diameter of the first portion 132 of the internal bore 130. In this manner, before the probe 102 is secured in place, the probe 102 may slide about the internal bore 130. This enables a user to position the probe 102 within the hot gas path 104 before securing the probe 102 in place.

In addition, the internal bore 130 may include a second portion 134 about the second end 126 of the main body 112 that is sized and shaped to house the compliant seal 114 and follower 116. For example, the outer diameter of the compliant seal 114 and follower 116 may be about the same size or slightly smaller than the diameter of the second portion 134 of the internal bore 130. The second portion 134 of the internal bore 130 may have a diameter greater than the first portion 132 of the internal bore 130. In some instances, the internal bore 130 may include a tapered portion 136 (or transition) between the first portion 132 of the internal bore 130 and the second portion 134 of the internal bore 130. The difference in diameter between the first portion 132 of the internal bore 130 and the second portion 134 of the internal bore 130 may cause the compliant seal 114 to become wedged about the tapered portion 136 of the internal bore 130, thereby filling in all voids between the internal bore 130 and the probe 102 so as to secure and seal the probe 102 within the main body 112 when the fastener 118 is tighten about the main body 112.

In certain embodiments, the main body 112 may include one or more cooling holes 138 in communication with the internal bore 130. In an example embodiment, the cooling holes 138 may be in communication with the first portion 132 of the internal bore 130. In this manner, the cooling holes 138 may provide cooling air to the internal bore 130 about the probe 102. The cooling air may cool the main body 112 and/or the probe 102. In some instances, the cooling holes 138 may be angled relative to the internal bore 130.

In order to secure the probe 102 within the main body 112 and to form a seal between the probe 102 and the main body 112, the compliant seal 114 may be positionable within the internal bore 130 about the probe 102. For example, the compliant seal 114 may include an aperture 140 for the probe 102 to pass through. The compliant seal 114 may be disposed within the second portion 134 of the internal bore 130 adjacent to the tapered portion 136 of the internal bore 130. Moreover, the follower 116 may be positionable within the internal bore 130 about the probe 102 and adjacent to the compliant seal 114. For example, the follower 116 may include a passage 142 for the probe 102 to pass through. The follower 116 may be disposed within the second portion 134 of the internal bore 130 adjacent to the compliant seal 114.

The fastener 118 may be attached to the second end 126 of the main body 112. The fastener 118 may include a first end 144 and a second end 146. The first end 144 of the fastener 118 (which may include threads) may be configured to mate with the second end 126 of the main body 118 (which may include corresponding threads). The fastener 118 also may include a cavity 148 and a lip 150. The cavity 148 may be configured to house a portion of the follower 116 when the fastener 118 is attached to the main body 112. In this manner, as the fastener 118 is attached to the main body 112, the follower 116 may at least partially nest within the cavity 148. The lip 150 of the cavity 148 may contact the follower 116 and force the follower 116 to press against the compliant seal 114. As the follower 116 presses on the compliant seal 114, the compliant seal 114 may compress and deform about the probe 102 and the tapered section 136 of the internal bore 130. The deformation of the compliant seal 114 about the probe 102 may lock the probe 102 in place within the main body 112 to prevent axial or radial movement of the probe 102. Moreover, the deformation of the compliant seal 114 about the probe 102 may form a seal about the probe 102 and the main body 112.

In this manner, threading the main body 112 and fastener 118 causes the follower 116 to engage the compliant seal 114 which deforms about the probe 102 within the main body 112 to secure and seal the probe 102 within the main body 112. Conversely, unthreading the main body 112 and fastener 118 causes the follower 116 to disengage the compliant seal 114 which in turn disengages the probe 102 to enable the probe 102 to be adjusted within the main body 112.

The tube 120 may be attached to the fastener 118 opposite the main body 112. The tube 120 may extend from the fastener 118. In some instances, the tube 120 may be integral with the fastener 118. The tube 120 may provide a passage 152 for connecting a sampling tube 154 to the probe 102. For example, the compression fitting 122 may be disposed about the tube 120. In some instances, the compression fitting 122 may be a Swagelok fitting or the like. The compression fitting 122 may provide a connection between the tube 120 and the sampling tube 154. The sampling tube 154 may provide a sealed path for remotely-located instrumentation 156 to be connected to the probe 102.

In some instances, the probe 102 may be ceramic. For example, the probe 102 may be made of a high-temperature ceramic material, such as silicon carbide. The ceramic probe 102 may include one or more passages 158 that pass through the ceramic probe 102, into the fitting 100, and out the sampling tube 154 to the remotely-located instrumentation 156. The ceramic probe 102 may provide a gas sample for emissions testing or may measure static or total pressure within the hot gas path 104.

In some instances, one or more components of the fitting 100, such as the main body 112, may be metal. For example, the main body 112 may be as stainless steel, Inconel, or Hastelloy-X. The main body 112 may be any material. In this manner, the fitting 100 provides a secure connection between a ceramic probe 102 and a metal fitting 100. In some instances, the compliant seal 114 may be made from a material with a low thermal conductivity (thermal insulator). The probe 102 may get extremely hot since it is exposed to the hot gas path 104. The only part of the fitting 100 in direct contact with the probe 102 is the compliant seal 114. By making the compliant seal 114 from a low thermal conductivity material, the amount of heat transferred to the metal fitting 100 may be minimized, which may prevent the metal from melting.

The fitting 100 may provide a sound joint between the probe 102 and the casing 106. The relatively gentle manner in which the compliant seal 114 "grabs" the probe 102 prevents cracking of the ceramic. Moreover, the cooling holes 138 in the main body 112 allow cooling air to flow within the main body 112, which may keep the fitting 100 below its melting temperature.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A fitting for positioning a probe in a hot gas path within a casing of a gas turbine engine, the fitting comprising:
    a main body comprising a first end and a second end, wherein the first end is attachable to the casing opposite the hot gas path, wherein the main body comprises an internal bore having a first portion about the first end, a second portion about the second end and a tapered portion disposed between the first portion and the second portion, wherein the second portion has a larger diameter than the first portion, wherein the main body comprises one or more cooling holes in communication with the first portion of the internal bore;
    a compliant seal positionable within the second portion of the internal bore;
    a follower at least partially positionable within the second portion of the internal bore adjacent to the compliant seal; and
    a fastener comprising a cavity and a lip, wherein the fastener is configured to mate with the second end of the main body, wherein the follower is at least partially disposed within the cavity, wherein the lip is configured to push the follower against the compliant seal, which deforms the compliant seal about the probe within the main body to secure and seal the probe within the main body.

2. The fitting of claim 1, further comprising a tube attached to the fastener opposite the main body.

3. The fitting of claim 2, further comprising a compression fitting disposed about the tube.

4. The fitting of claim 3, further comprising a sampling tube in communication with the compression fitting.

5. The fitting of claim 1, wherein the probe is positionable within the internal bore.

6. The fitting of claim 1, wherein the compliant seal comprises an aperture for the probe to pass through.

7. The fitting of claim 1, wherein the follower comprises a passage for the probe to pass through.

8. The fitting of claim 1, wherein the probe is a ceramic probe.

9. The fitting of claim 1, wherein the main body is threaded to the casing.

10. The fitting of claim 1, wherein the main body and the fastener are threaded together.

11. The fitting of claim 10, wherein threading the main body and fastener causes the follower to engage the compliant seal which deforms about the probe within the main body to secure and seal the probe within the main body.

12. The fitting of claim 10, wherein unthreading the main body and fastener causes the follower to disengage the compliant seal which in turn disengages the probe to enable the probe to be adjusted within the main body.

13. The fitting of claim 1, wherein the main body is formed of metal.

14. The fitting of claim 1, wherein the one or more cooling holes are angled relative to the internal bore.

15. A method of positioning a probe in a hot gas path within a casing of a gas turbine engine, the method comprising:
    attaching a main body to the casing opposite the hot gas path, wherein the main body comprises a first end and a second end, wherein the first end is attachable to the casing opposite the hot gas path, wherein the main body comprises an internal bore having a first portion about the first end, a second portion about the second end, and a tapered portion disposed between the first portion and the second portion, wherein the second portion has a larger diameter than the first portion, wherein the main body comprises, one or more cooling holes in communication with the first portion of the internal bore;
    positioning the probe within the internal bore;
    positioning a compliant seal within the second portion of the internal bore about the probe;
    positioning a follower at least partially within the second portion of the internal bore about the probe and adjacent to the compliant seal;
    adjusting a fastener attached to the second end of the main body, wherein the fastener comprises a cavity and a lip, wherein the follower is at least partially disposed within the cavity, wherein the lip is configured to push the follower against the compliant seal; and
    deforming the compliant seal about the probe within the main body to secure and seal the probe within the main body.

16. An assembly for taking measurements in a hot gas path within a casing of a gas turbine engine, the assembly comprising:
    a ceramic probe; and
    a fitting for positioning the ceramic probe in the hot gas path within the casing of the gas turbine engine, the fitting comprising:
        a main body comprising:
            a first end and a second end, wherein the first end is attachable to the casing of the gas turbine engine opposite the hot gas path;
            an internal bore extending from the first end to the second end, wherein the internal bore comprises a first portion about the first end, a second portion about the second end, and a tapered portion disposed between the first portion and the second portion, wherein the second portion has a larger diameter than the first portion, wherein at least a portion of the ceramic probe is positionable within the internal bore; and
            one or more cooling holes in communication with the first portion of the internal bore;
        a compliant seal positionable within the second portion of the internal bore about the ceramic probe;
        a follower at least partially positionable within the second portion of the internal bore about the ceramic probe and adjacent to the compliant seal; and
        a fastener comprising a cavity and a lip, wherein a first end of the fastener is configured to mate with the second end of the main body, wherein the follower is at least partially disposed within the cavity, wherein the lip is configured to push the follower against the compliant seal, which deforms the compliant seal to secure and seal the ceramic probe within the main body.

17. The assembly of claim 16, further comprising a tube attached to the fastener opposite the main body.

18. The assembly of claim 17, further comprising a compression fitting disposed about the tube.

19. The assembly of claim 18, further comprising a sampling tube in communication with the compression fitting.

* * * * *